US012226533B2

(12) United States Patent
Natale et al.

(10) Patent No.: US 12,226,533 B2
(45) Date of Patent: Feb. 18, 2025

(54) SILICA MODIFIED VATERITE JANUS DRUG DELIVERY PARTICLES

(71) Applicant: UTI LIMITED PARTNERSHIP, Calgary (CA)

(72) Inventors: Giovanniantonio Natale, Calgary (CA); Harsovin Kaur, Calgary (CA)

(73) Assignee: UTI LIMITED PARTNERSHIP, Calgary (CA)

( * ) Notice: Subject to any disclaimer, the term of this patent is extended or adjusted under 35 U.S.C. 154(b) by 756 days.

(21) Appl. No.: 17/296,349

(22) PCT Filed: Dec. 2, 2019

(86) PCT No.: PCT/CA2019/051725
§ 371 (c)(1),
(2) Date: May 24, 2021

(87) PCT Pub. No.: WO2020/113317
PCT Pub. Date: Jun. 11, 2020

(65) Prior Publication Data
US 2022/0096390 A1   Mar. 31, 2022

Related U.S. Application Data

(60) Provisional application No. 62/775,097, filed on Dec. 4, 2018.

(51) Int. Cl.
| | | |
|---|---|---|
| A61K 9/51 | (2006.01) | |
| A61K 9/14 | (2006.01) | |
| B82Y 5/00 | (2011.01) | |
| B82Y 30/00 | (2011.01) | |
| B82Y 40/00 | (2011.01) | |
| C01F 11/18 | (2006.01) | |

(52) U.S. Cl.
CPC ............ *A61K 9/5115* (2013.01); *A61K 9/143* (2013.01); *C01F 11/18* (2013.01); *B82Y 5/00* (2013.01); *B82Y 30/00* (2013.01); *B82Y 40/00* (2013.01); *C01P 2002/72* (2013.01); *C01P 2004/03* (2013.01); *C01P 2004/64* (2013.01)

(58) Field of Classification Search
CPC ....... A61K 9/5115; A61K 9/143; C01F 11/18; B82Y 5/00; B82Y 30/00; B82Y 40/00; C01P 2002/72; C01P 2004/03; C01P 2004/64; A61P 35/00
See application file for complete search history.

(56) References Cited

FOREIGN PATENT DOCUMENTS

CN   106084215 A  *  11/2016

OTHER PUBLICATIONS

Zou et al., "Sodium Silicate route to coat polymer particles with silica," Colloid and Polymer Science, 2014, vol. 292, pp. 1693-1700. (Year: 2014).*

(Continued)

*Primary Examiner* — Benjamin J Packard
*Assistant Examiner* — Joshua A Atkinson
(74) *Attorney, Agent, or Firm* — FisherBroyles LLP; Anthony J DoVale; Richard Echler

(57) ABSTRACT

Silica modified vaterite Janus nanoparticles are provided, together with methods for the synthesis of such particles. The disclosed methods make use of a Pickering emulsion, in a scalable aqueous process. The silica-modified surface is amenable to chemical modification, for example with physiologically acceptable labels.

5 Claims, 3 Drawing Sheets

(56) References Cited

OTHER PUBLICATIONS

Graf et al., "A General Method to Coat Colloidal Particles with Silica," Langmuir, 2003, vol. 19, pp. 6693-6700. (Year: 2003).*
Saad et al., "Scalable Chemical Synthesis Route to Manufacture pH-Responsive Janus CaCO3 Micromotors", 2020, Langmuir, 36, pp. 12590-12600. (Year: 2020).*
Cui et al., Langmuir, Nov. 21, 2012, 28, pp. 314-320. 1-10.
Dunuweera et al., J. Nanomed. Biother. Dis., Jul. 28, 2017, vol. 7(1): 1000150, pp. 1-9. 1-10.
Dunuweera and Rajapakse, 2018 Biomed. Phys. Eng. Express 4 015017.
Guix et al., Sei. Report, Feb. 24, 2016, 6: 21701, pp. 1-7.
Khoee, S., & Nouri, A. (2018). Preparation of Janus nanoparticles and its application in drug delivery. Design and Development of New Nanocarriers, 145-180.
Liu et al. J Mater Chem B Mater Biol Med. Nov. 14, 2015; 3(42): 8314-8320.
International Search Report & Written Opinion dated Feb. 24, 2021 for International Application No. PCT/CA2019/051725.

* cited by examiner (a)

(b)

SILICA MODIFIED VATERITE JANUS DRUG DELIVERY PARTICLES

FIELD

Biocompatible drug delivery formulations are disclosed, formed of calcium carbonate nanoparticles having a patterned silica-modified surface, together with methods for forming such particles and uses thereof.

BACKGROUND

Calcium carbonate occurs in a number of crystalline polymorphs: calcite, argonite and vaterite. Each of these polymorphs have distinct physiochemical characteristics. It has for example been suggested that encapsulating drugs in porous nanoparticles of vaterite may facilitate drug release in the vicinity of cancer cells by virtue of the relatively low solubility of vaterite at slightly acidic pH in cancerous tissues and the relative insolubility of vaterite in neutral and slightly basic pH conditions of blood and healthy tissues (Dunuweera and Rajapakse, J Nanomedine Biotherapeutic Discov 2017, Vol 7(1); and, Dunuweera and Rajapakse, 2018 Biomed. Phys. Eng. Express 4 015017). Similarly, surface modified vaterite nanoparticles adapted for drug delivery have been disclosed (Liu et al. J Mater Chem B Mater Biol Med. 2015 Nov. 14; 3(42): 8314-8320).

Janus particles are a class of nanoparticles that have physically or chemically distinct surfaces, and this characteristic may serve as the basis for tailoring drug delivery systems (Khoee, S., & Nouri, A. (2018). Preparation of Janus nanoparticles and its application in drug delivery. Design and Development of New Nanocarriers, 145-180). It has for example been suggested that calcium carbonate Janus particles might be adapted for drug delivery to tumor cells (Guix et al., Sci Rep. 2016; 6: 21701).

There remains a need for optimized biocompatible drug delivery systems.

SUMMARY

Silica modified vaterite Janus nanoparticles are provided, together with methods for the synthesis of such particles. The disclosed methods make use of a Pickering emulsion, in a scalable aqueous process. The silica-modified surface is amenable to chemical modification, for example with physiologically acceptable labels.

DETAILED DESCRIPTION

Figure 1:
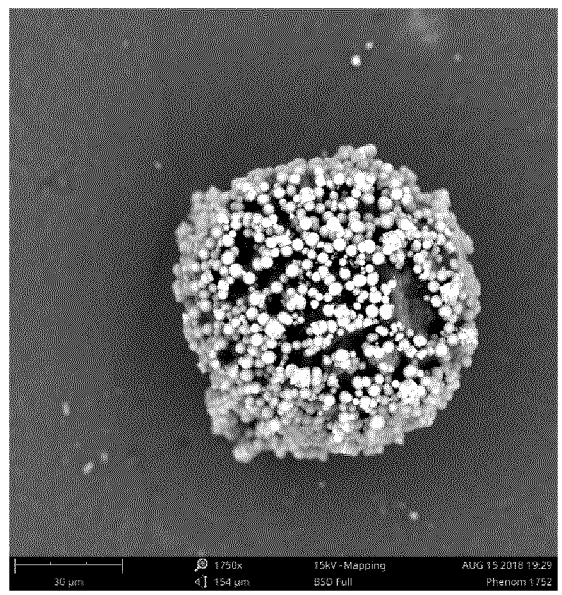
FIG. 1 is a SEM image of the exemplified Pickering emulsion.

In one aspect, the present innovations provide processes for the formation of $CaCO_3$ Janus particles, including steps of:
 synthesis of vaterite $CaCO_3$ nanoparticles;
 formation of a Pickering emulsion comprising the vaterite particles on the surface of wax phase droplets;
 selective surface silicate modification of the vaterite particles in the Pickering emulsion; and,
 dissolution of the wax phase droplets to provide silica modified vaterite Janus particles.

Processes may for example involve encapsulating a biologically active compound in the vaterite $CaCO_3$ nanoparticles prior to formation of the Pickering emulsion. Alternatively, processes may further include steps of modifying a silicate surface of the silica modified vaterite Janus particles, for example to attach a physiologically acceptable label to the silicate surface.

The silica modified vaterite Janus particles may for example be used in methods for preferentially delivering an encapsulated biologically active compound to a target tissue in a subject in need thereof. The biologically active compound may for example be a chemotherapeutic agent, and the subject may for example have a cancer and the target tissue may be a solid tumor.

In select embodiments, synthesis of $CaCO_3$ Janus particles may be carried out using biologically compatible solvents, particularly in the context of Pickering emulsion formation. This may facilitate both the formulation of such particles in a physiologically acceptable form, as well as providing an ecologically benign synthetic protocol.

An exemplary embodiment is described below.

Synthesis of $CaCO_3$ Janus Particles

In this example, there are four steps involved in the formation of $CaCO_3$ Janus particles: i) synthesis of $CaCO_3$ microparticles, ii) formation of a Pickering emulsion, iii) half surface modification of particles, and iv) dissolution of wax.

Materials

Calcium Chloride ($CaCl_2$), Sodium Carbonate ($Na_2CO_3$), Dimethyl sulfoxide (99.9% purity), 23 wt % Sodium silicate ($Na_2SiO_3$) solution, n-eicosane (99%) were purchased from Sigma Aldrich. The water used in this example was purified using Milli-Q system.

Synthesis of $CaCO_3$ Microparticles Particles

Vaterite $CaCO_3$ microparticles were obtained precipitation, wherein 0.3M aqueous solution of $NaCO_3$ was stirred using magnetic stirrer and an equal volume of equimolar solution of $CaCl_2$) was added to it at once. The resulting reaction mixture was subjected to continuous stirring for 15 mins at 600 rpm. The particles thus obtained were washed five times with deionized water to remove excess sodium and chloride ions remaining in solution. The synthesized particles were dried and stored in powder form under dry conditions.

Formation of Pickering Emulsion 0.01 wt % of vaterite $CaCO_3$ particles were dissolved in $DMSO:H_2O$ (1:12) solution and, to prevent the particles from aggregating, the solution was exposed to ultrasound using a bath sonicator. The suspension was then heated along with vigorous stirring until the temperature of the solution reached 38° C. Thereafter, 0.04 wt % of n-eicosane was added to the heated solution and stirred rapidly for 20 mins. The emulsion was then allowed to cool at room temperature, the wax upon cooling solidifies and entraps vaterite $CaCO_3$ particles in the water and oil interface, forming a Pickering emulsion. Excess of wax is filtered out, and the extracted solid phase washed with $DMSO:H_2O$ (1:12) solution.

Surface Modification Using Sodium Silicate 0.03 wt % sodium silicate solution was added to the resulting Pickering emulsion. The suspension obtained was stirred at 600 RPM for 40 mins, producing surface modified vaterite particles. The surface modified Pickering emulsion was separated out and washed twice with DMSO:$H_2O$ (1:12) solution to remove excess silica from solution. FIG. 1 is a SEM image of the obtained Pickering emulsion.

Dissolution of Wax

Figure 2:
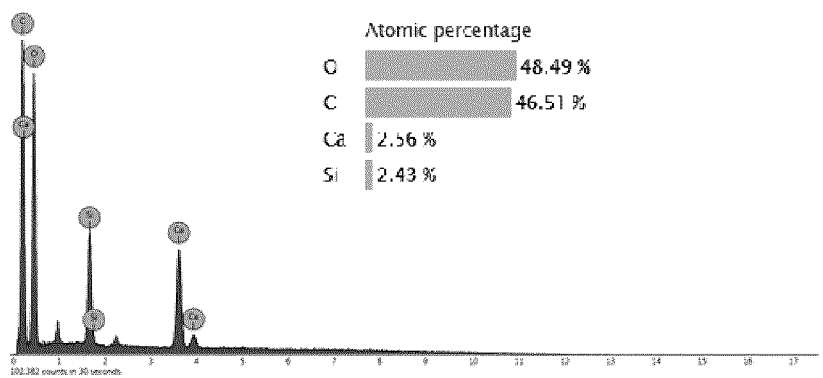
FIG. 2 is a graph illustrating energy-dispersive X-ray spectroscopy (EDX) data of synthesized silica modified vaterite $CaCO_3$ Janus particles.

Pickering emulsion dispersed in DMSO:$H_2O$ (1:12) solution was exposed to sonication for 1 min to separate the surface modified particles from wax spheres. The wax spheres in the mixture were then melted by heating the solution at 50° C. until the entire wax phase formed a layer floating on the surface of the aqueous phase. The solution was then allowed to cool and settle for 20 mins. The surface modified particles suspended in the lower layer were filtered out and dried under vacuum. The particles thus extracted are silica modified vaterite $CaCO_3$ Janus particles. FIG. 2 is a graph illustrating EDX data of synthesized silica modified vaterite $CaCO_3$ Janus particles.

Motion of $CaCO_3$ Janus Particles Under Different pH Conditions

In use, a feature associated with the present vaterite Janus particles is active propulsion, based on the formation of chemical gradients generated by the dissociation of the surface carbonate system in the presence of an acidic medium—leading to formation of $HCO_3^-$ (major product), $H^+$ and $OH^-$. The $HCO_3^-$ thus formed may further dissociate to evolve $CO_2$. The overall reaction can be represented as:

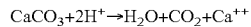

$$CaCO_3 + 2H^+ \rightarrow H_2O + CO_2 + Ca^{++}$$

Figure 3:
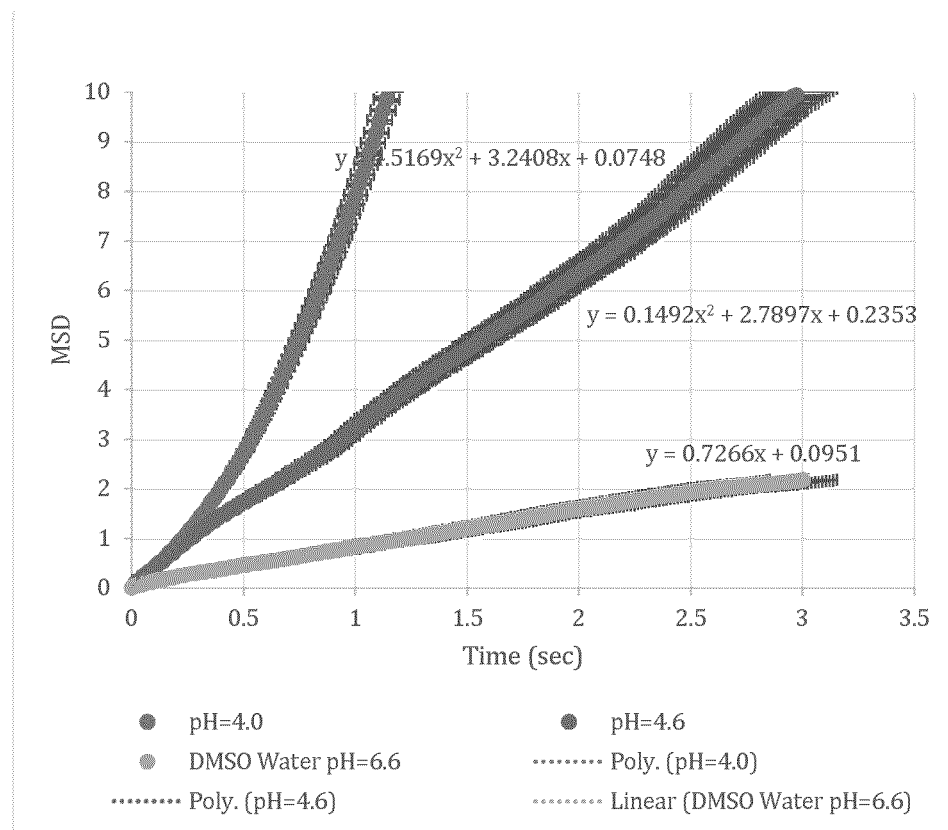
FIG. 3 is a graph illustrating the MSD of $CaCO_3$ Janus particles under different pH conditions.
Figure 4:
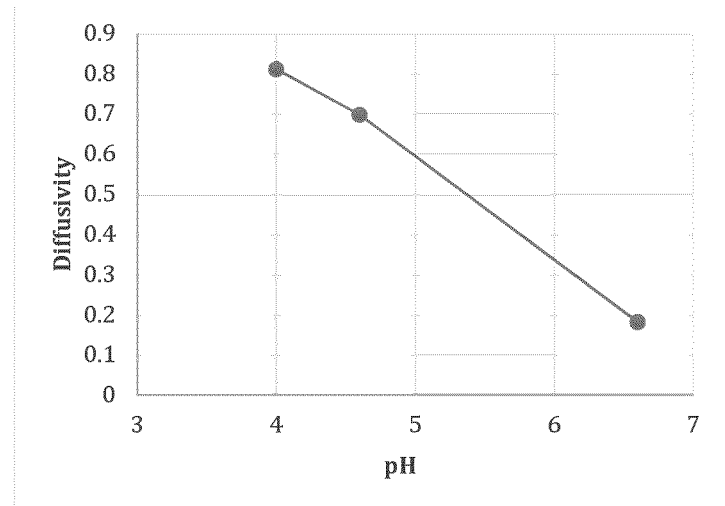
FIG. 4 includes two graphs, illustrating (a) diffusivity (b) velocity of the asymmetric $CaCO_3$ particles at different pH.
Figure 4:
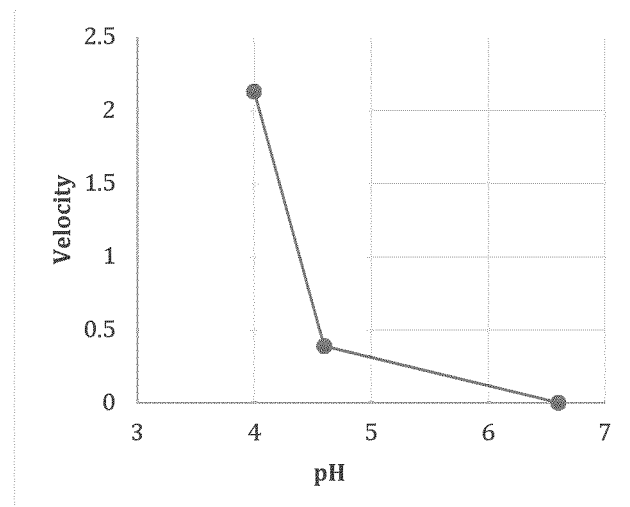

On this basis, diffusion-osmosis was used to trigger the motion of $CaCO_3$ Janus particles under different pH conditions. FIG. 3 represents the MSD data obtained on analysis of $CaCO_3$ Janus particles under alternative pH conditions, where simple Brownian motion of the asymmetric $CaCO_3$ particles was observed at pH of 6.6. Active propulsion was obtained on addition of acid to the system, wherein MSD of the particles was increased with the decrease in pH. FIG. 4 includes two graphs, illustrating (a) diffusivity (b) velocity of the asymmetric $CaCO_3$ particles under different pH conditions.

The invention claimed is:

1. A process for the formation of $CaCO_3$ Janus particles comprising:
   synthesizing vaterite $CaCO_3$ nanoparticles;
   suspending the vaterite $CaCO_3$ nanoparticles in dimethyl sulfoxide (DMSO), to form a suspension of vaterite $CaCO_3$ nanoparticles in DMSO;
   mixing a wax phase with the suspension of vaterite $CaCO_3$ nanoparticles in DMSO to form a Pickering emulsion comprising the vaterite particles on the surface of wax phase droplets;
   selectively modifying a silicate surface of the vaterite particles in the Pickering emulsion; and,
   dissolving the wax phase droplets to provide silica modified vaterite Janus particles.

2. The process of claim 1, further comprising encapsulating a biologically active compound in the vaterite $CaCO_3$ nanoparticles prior to formation of the Pickering emulsion.

3. The process of claim 1, further comprising modifying a silicate surface of the silica modified vaterite Janus particles.

4. The process of claim 3, wherein modifying the silicate surface comprises attaching a physiologically acceptable label to the silicate surface.

5. The process of claim 2, wherein the biologically active compound is a chemotherapeutic agent.

* * * * *